United States Patent [19]

Barber

[11] 4,243,026
[45] Jan. 6, 1981

[54] FINGER SPLINT

[76] Inventor: Lois M. Barber, 111 Nieto Ave., Long Beach, Calif. 90803

[21] Appl. No.: 948,869

[22] Filed: Oct. 5, 1978

[51] Int. Cl.³ .............................................. A61F 5/10
[52] U.S. Cl. .................................... 128/77; 128/87 A
[58] Field of Search ................................ 128/87 A, 77

[56] References Cited

U.S. PATENT DOCUMENTS

| 3,170,460 | 2/1965 | Stilson | 128/77 |
| 3,595,225 | 7/1971 | Beeman | 128/77 |

FOREIGN PATENT DOCUMENTS

| 929317 | 6/1963 | United Kingdom | 128/87 A |
| 1346181 | 2/1974 | United Kingdom | 128/77 |

OTHER PUBLICATIONS

Glanville, H.J., *New Inventions*, pp. 252-253 of The Lancet, Feb. 3, 1962.
*Orthopaedic Appliances Atlas*, vol. 1, pub. by J. W. Edwards, Ann Arbor Mich., 1952, pp. 303-305, 312, 314, 315.

*Primary Examiner*—Robert W. Michell
*Assistant Examiner*—Arthur S. Rose
*Attorney, Agent, or Firm*—George F. Bethel; Patience K. Bethel

[57] ABSTRACT

An adjustable finger splint made entirely of a single piece of spring steel wire which is bent into a configuration which includes a central arcuate section adapted to cup a portion of the circumferential curve of one of the dorsal and ventral surfaces of a finger or thumb. A pair of substantially arcuate arms extend in opposite directions from the ends of the central section in a lengthwise manner generally following the anatomical conformation of a finger which is to be splinted. A pair of arcuate support pieces in a somewhat rectangular shape are formed from the terminal ends of the arms. These support pieces are designed to cup the part of the finger into which they are in contact. The splint is worn with the terminal arm support pieces either under the finger for extension of the finger, or the terminal arm support pieces can be worn on the top of the finger for flexion of the finger. Heat sealed foam pads cover the central arcuate section and the terminal arm support pieces for comfort. Exposed parts of the spring steel are encased in a teflon sleeve. The spring steel wire of which the finger splint is constructed permits individualized fit through bending, as well as motion of the finger to be splinted. All of the fingers of the hand, including the thumb, can be splinted using the finger splint of the invention.

7 Claims, 11 Drawing Figures

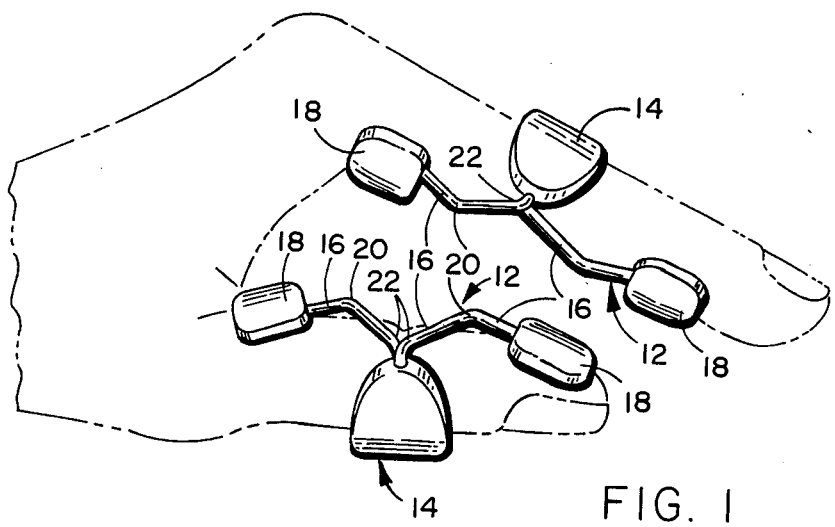
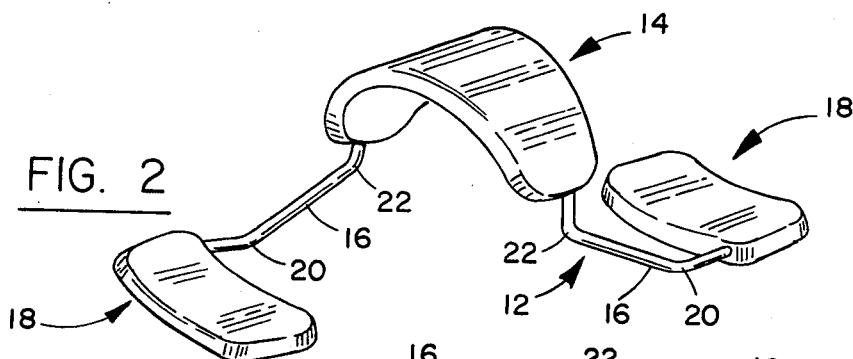
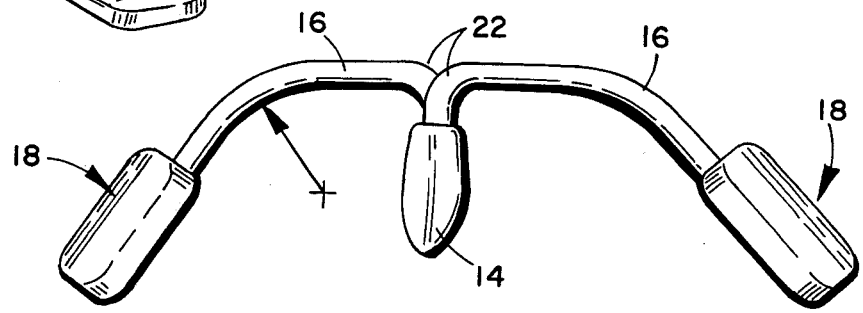
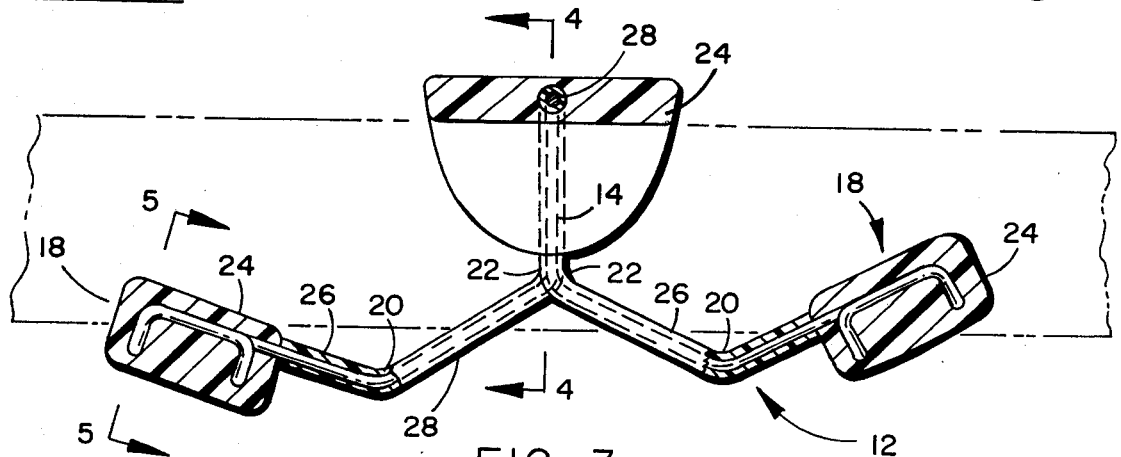

FINGER SPLINT

BACKGROUND OF THE INVENTION

1. Field of the Invention

This invention relates to the field of orthotics, and particularly to the splinting of fingers whereby a lightweight finger splint constructed of a single piece of bent spring steel wire which is covered with foam pads, permits the extension and flexion splinting of one or all of the fingers of the hand, including the thumb.

2. Description of the Prior Art

The splinting of hands and fingers is often used in rehabilitating arthritic patients, stroke and accident victims and the like having neurological, muscle, joint and tendon damage in order to restore mobility to the fingers and joints of the hand. In all cases, it is desirable that the finger splints be easily conformed to the user's hands and at the same time be capable of further adjustment when the desired degree of flexion or extension of the finger, for example, has been achieved. At this point, for example, it would be desirable to further splint the finger for a greater corrective force to be applied to the finger.

Most desirably, such a finger splint would be capable of allowing mobility of the fingers while it is exerting a force. Further, the splint should be readily removable for the above mentioned readjustment to permit baths and for patient comfort. Other desirable features include a splint which is not restrictive of other uninvolved joints of the fingers or hand, so that use of the hand is possible during the course of corrective splinting.

A splint which is well ventilated is another desirable feature, so that increased temperature is not a comfort problem. Further, the finger splint should be constructed of a strong, long lasting material which will not be readily subject to rust or other types of deterioration during the use of the splint. Adequate padding of the finger splint, as well as lightness in weight are also extremely desirable characteristics to provide maximum comfort to the patient. It is also desirable that the finger splint be capable of being washed which requires a washable type of exterior material.

The ideal finger splint is also one which can be readily placed on the finger and removed easily by the patient, so that outside help is not required. This can be of considerable help to patients who are severely lacking in finger mobility for more than one of their fingers. Any difficulty of emplacement of the splint can represent a considerable amount of frustration for the patient.

Finger splints which are utilized at the present time include flat rigid materials, such as metal or wood used in conjunction with adhesive tape and in some cases removable types of strapping material. This type of splint completely immobilizes the finger. While this might be desirable in certain cases, such as when fingers are being splinted after a bone breakage, they are not desirable for use with patients who need some movement in order to prevent joint contractures or stiffening. Furthermore, they are not adaptable for both the flexion and extension splinting of a finger.

Other types of splints are complicated affairs using many wires, combinations of wires, pads and straps in combination with rubber bands, hooks and the like. While such splints have enjoyed some success, their design and straps make them cumbersome for application by the patient. The projections can be a hazard and they also prevent use of the finger. More importantly, such splints are not usable for splinting of the thumb.

Until the present time, there has not been available for finger splinting, an adjustable finger splint which is well ventilated, soft and strong, yet light in weight, having long lasting parts, usable for overcoming flexion and extension, contractures of joints, while allowing mobility of the splinted finger and uninvolved fingers and which can be used for flexion and extension splinting of thumbs.

SUMMARY OF THE INVENTION

The novel adjustable finger splint of the invention combines the strength, light weight, springy and bendable characteristics of spring steel with the soft, flexible nature of polyethylene foam at the points of finger contact. The finger splint is designed in a novel manner which allows for infinite adjustment of the finger splint for various stages of flexion and extension pressure. Further adjustment is easily made using the same splint when the affected joint is in the course of correction. All the initial and subsequent adjustment of the splint can be made by hand bending of the splint with the possible occasional aid of a pair of hand held pliers.

As used herein and in the appended claims, the use of the term "finger" is meant to include all digits of the hand, including the thumb unless separately identified.

The splint is formed of a continuous piece of spring steel wire which is bent into a central section which either underlies or overlies the finger, depending upon its use. A pair of arms extend in opposite directions from the ends of the central arcuate section. The ends of the arms terminate in another substantially rectangular shaped arcuate section which acts as a support piece. The central section and terminal arm support sections are covered with a foam padding material.

By placing the central arcuate section under the proximal interphalangeal joint of the finger with the terminal arm support pieces worn on the dorsal or upper surface of the finger, the splint becomes usable for providing a desired degree of flexion to a finger. This is controlled by appropriately bending the arm to the desired angle of comfort and pressure desired.

The splint can be used to provide extension to a finger which is in a contracted state by rotating the splint one hundred and eighty degrees so that the arcuate curved central section overlies the proximal interphalangeal joint on the dorsal or upper surface of the finger. The terminal arm support pads are then employed on the ventral or under surface of the finger and the support arms are appropriately bent to provide the desired force.

Similar positioning of the splint on a thumb can provide flexion or extension, depending upon how it is emplaced on the finger.

The advantages of such a splint are immediately obvious. The ability of the same basic splint to be used as an extension or flexion splint provides reduced manufacturing costs, since differently designed splints are not required. This is also true for the capability of use of the splint on all of the fingers of the hand, including the thumb. Up to this time, it has been difficult to splint the thumb without impeding the thenar eminance or palm-thumb muscles. Such prior splinting resorted to cumbersome hand and wrist attachments.

By making the splint of a bendable type of material, it is very readily and easily bent to adjust for individual fit. Convenience and time savings for the fitter and comfort and time savings for the patient is thus provided.

The finger splint design, which will be apparent from the discussion to follow, is readily emplaced on the finger of a patient so that it can be easily put on and taken off at the desire of the patient for purposes of exercise or positioning. Also, the splint, being of such a simple design, is well ventilated, which minimizes any discomfort which might be encountered in warm weather due to the small amount of finger contact which is required for use of the finger splint.

The springy nature of the spring steel of which the splint is formed, permits exercising of the finger, that is to say, movement against the constant force which is applied by the spring. This permits exercising of the finger against the force, so that the finger may be used, even while it is being splinted. Of special note is the fact that the use of the finger splint of the invention does not interfere with the motion of unaffected fingers. This is important in allowing the patient to use healthy joints. An additional advantage of the open design of the splint is that swelling of the finger, which occasionally occurs during splinting, does not ordinarily interfere with the splinting action, since the points of contact are generally restricted to three points on the finger. Also, there is no circumferential pressure around the finger.

The polyethylene foam cushions or pads which enclose and cushion the points of finger contact avoid pressure problems. The foam is also soil resistant and is easily washed if necessary.

The spring steel where it is exposed and not covered by the polyethylene padding is preferably encased in a sleeve of polyethylene plastic to provide a smooth surface, as well as to improve the looks and provide a degree of non-soiling characteristics to the splint.

The adjustable finger splints of the invention have been found to be useful in the treatment of arthritic patients and patients recovering from burns, brachialplexus injury and traumatic hand injuries involving the tendons, joints, nerves and muscles of the fingers.

BRIEF DESCRIPTION OF THE DRAWINGS

The invention will be more clearly understood by reference to the description below taken in conjunction with the accompanying drawings wherein:

FIG. 1 shows a perspective elevation of the adjustable finger splint of the invention shown as an extension splint emplaced on an index finger and a thumb;

FIG. 2 shows a perspective view of the extension finger splint of the invention;

FIG. 3 shows an enlarged fragmented sectional view of the extension splint shown in FIGS. 1 and 2;

FIG. 5 shows a sectional view of the terminal arm support piece taken through lines 5—5 of FIG. 3;

DETAILED DESCRIPTION OF THE DRAWINGS

Figure 10:
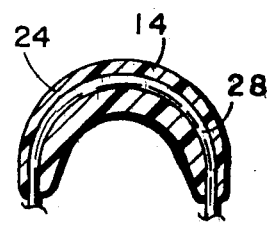
FIG. 10 shows a section of the central section of FIG. 7 taken along lines 10—10; and, FIG. 11 shows a slightly different embodiment of the adjustable finger splint of the invention.

In the drawings, FIGS. 1 through 5 show the adjustable finger splint 12 of the invention which has been bent to provide an extension finger splint, while FIGS. 6 through 11 show the adjustable finger splint 13 of the invention bent in such a way as to provide an extension splint as will be explained in the following description.

Figure 8:
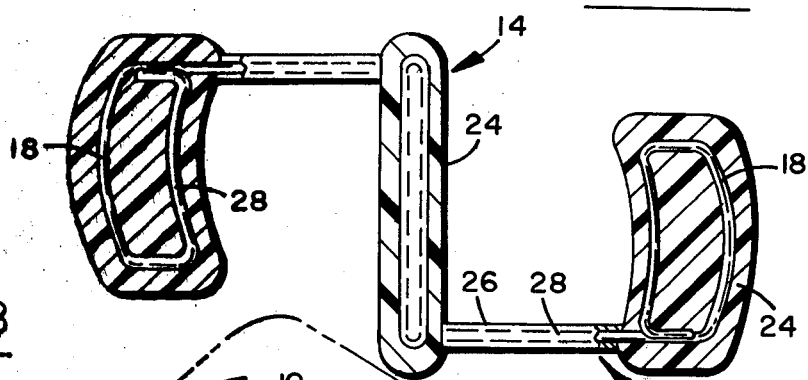
FIG. 8 shows a fragmented sectional view taken in the direction 8—8 of FIG. 7.

The splint is formed of a single piece of spring steel wire, as can be seen in FIGS. 3 and 8 in greater detail. The wire is bent at the midsection 14 to form the curved center section which is of a size and shape which is adapted to cup the upper or lower side of a finger. Extending from the center section 14 in opposite directions, conforming to the lengthwise contour of a finger are arms 16. The arms 16 are bent at points 22 and 20 and are then bent at the ends thereof into a curved substantially rectangular support section 18. The support sections 18 can be readily seen in detail in FIGS. 3, 5, 7 and 8.

Figure 4:
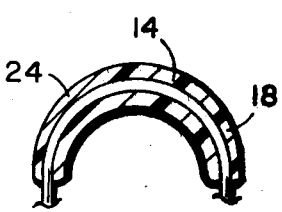
FIG. 4 shows a sectional view taken through the central section of the splint in the direction 4—4 of FIG. 3.
Figure 7:
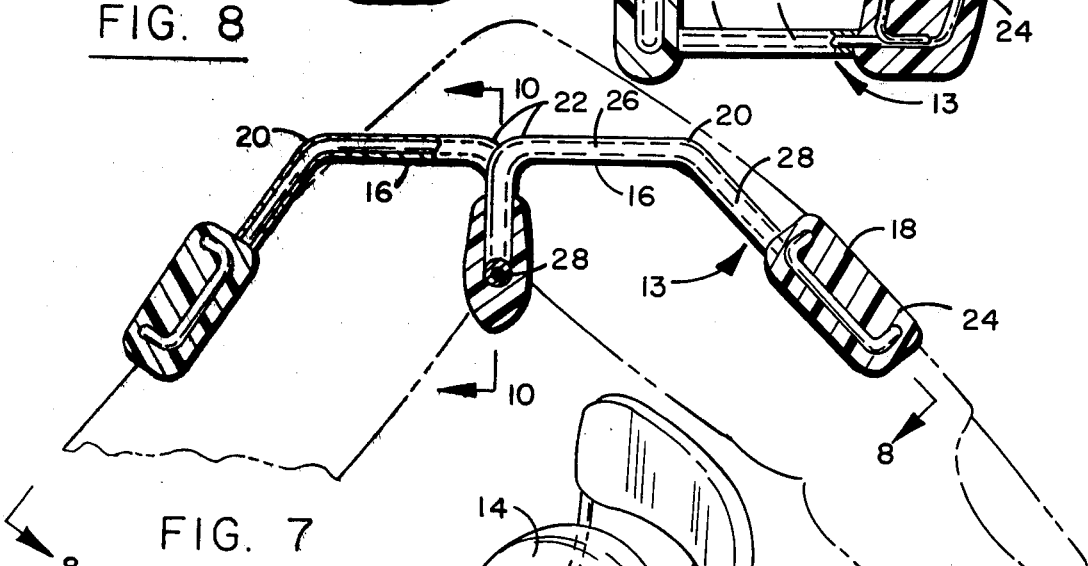
FIG. 7 shows a fragmented sectional view of the flexion splint of FIG. 6.

As shown in the fragmented sections of FIGS. 3, 7 and 8, as well as the sectional views of FIGS. 4 and 10, it can be seen that support pads of flexible heat sealed cushioning material 24 is adhered to and encloses the central section 14, as well as the terminal end support sections 18. Foamed polyethylene is the preferred material for this purpose.

In the exposed areas of the spring steel wire of the arms 16 there is a sleeve of flexible plastic 26 which completely encases the steel wire 28, as shown in FIG. 3. Teflon is preferred for this purpose.

The terminal arm support sections 18 which are covered with the foam plastic 24, preferably heat sealed polyethylene, are bent to a curve as shown in FIGS. 5 and 8 in a manner which is designed to cup and hold a side of a finger. In this instance, as well as in the curve of central section 14, the interior wire 28 and the overlayer of cushioned plastic 24 permit personalized adjustment by bending of these areas to give the best possible fit, as well as providing comfort to the patient.

Figure 6:
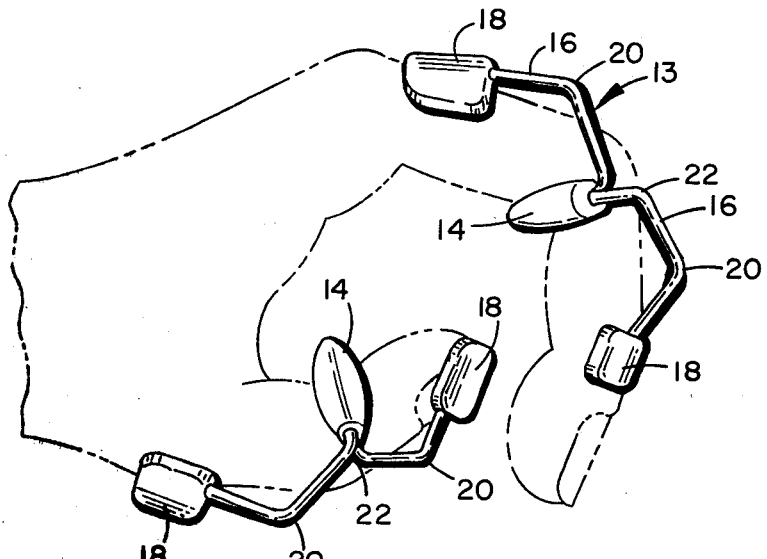
FIG. 6 shows a perspective elevation of the adjustable finger splint of the invention which has been bent to provide a flexion splint and emplaced on a thumb and index finger.

It is important to note that the adjustable finger splint 12 of the invention, as shown in FIGS. 1 through 5, and the splint 13 shown in FIGS. 6 through 11, are precisely the same splint. The only difference lies in the angles 20 and 22 which are bent to a greater or lesser degree, together with the amount of cushioning material surrounding the central curved section 14. The cushioning material is wider in the central section 14 in the case of the finger splint to be used as an extension splint to give greater comfort. The cushioning material is somewhat narrower in the central section 14 for the finger splint to be used as a flexion splint as shown in FIG. 6 so that the fingers can more readily bend over the cushioning material. In every other respect, the finger splint is the same.

The wider cushioning of the central section 14 of the adjustable finger splint 12 which is used an an extension splint, can be seen in FIGS. 1, 2, 3 and 4. The narrower cushioning of the central section 14 of the adjustable finger splint 13 can be seen in FIGS. 6 through 10.

When the splint is to be used as an extension splint, the splint is placed on the finger with the terminal arm support sections 18 emplaced on the ventral or underside of the finger as shown in FIG. 1. At the same time, the center curved section 14 is placed on the dorsal or back side of the fingers substantially over the proximal interphalangeal joint in the case of the fingers and over the interphalangeal joint in the case of the thumb. When placed on the fingers, the support pads 18 provide a force against bending to the finger, while at the same time allowing movement of the uninvolved joints.

It is important to note in this instance, that the splint is bent at points 22 and 20 so that a strong but gentle pressure is being exerted against forces by the finger. The amount of pressure is controlled by increasing or decreasing the angles at 20 and 22.

In the case of the extension splint 12 as shown in FIGS. 1 through 5, the angles at points 20 and 22 are greater, that is to say, more obtuse, than those found in the flexion splint 13 of FIGS. 6 through 10. Basically, any angle which gives the desired force to the finger for the purposes for which the splint is to be used, is adequate for use of the splint. Thus, it would be possible to bend point 22 in some instances more than at point 20 with the same result.

Figure 9:
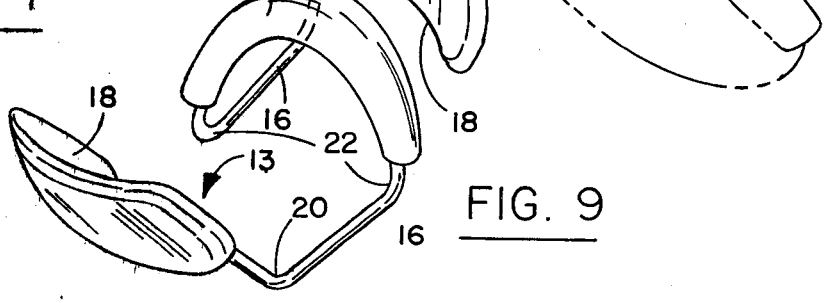
FIG. 9 shows a perspective view of the flexion finger splint of the invention.

It should be also noted as can be seen best in FIG. 9, for example, that at angle 22 of the arms 16 it is desirable to slightly bend the wire 28 inwardly of the central axis to give in some instances, a better finger cupping action to the splint.

When the finger splint 13 of the invention is to be used as a flexion splint, as shown in perspective at FIG. 9, the splint is placed on the finger, as shown in FIG. 6. Specifically, the central section 14 is placed on the ventral or underside of the finger substantially under the proximal interphalangeal joint of the finger and under the interphalangeal joint of the thumb as shown in FIG. 6. The terminal arm support sections 18 are then worn on the dorsal or backside of the finger as shown in FIG. 6.

As mentioned previously, the foam cushioning 24 sandwiched over the central curved section 14 of the splint is wider in the case of the splint to be used as an extension splint 12 as shown in FIG. 2 than would be used for a flexion splint 13 as shown in FIG. 9. However, it should be noted that the curve of the wire 28 within each of the bent configurations is precisely the same, as can be seen at 14 in FIG. 3, and in FIG. 8, and more particularly in the sections shown in FIGS. 4 and 10. The differences in width of foam improve comfort and support of the splint.

As mentioned above, the angle at points 22 and 20 of the arm 16 determine whether the splint is usable as a flexion or an extension splint. The exact angle for these points is not critical, except to the extent that the fingers should be held in a position which is consonant with the desired splinting effort to be made. This would have to be determined on an empirical basis, depending upon the extent of the injury to be treated as well as the size of the hand and the specific conformation of the finger. It has been found, however, that the angles as shown in the drawings form a good starting point to begin adjustment for purposes of fitting individual fingers.

As an alternative to the angle at point 20, for a splint to be used as an extension or flexion splint, there is shown an alternative embodiment in FIG. 11. Specifically where the arrow is shown, the angle is eliminated and is replaced with a gradual curve from point 22 to the terminal arm support pieces 18. This embodiment is not as preferred as that shown in FIG. 2, simply because it is slightly more difficult to adjust the actual bend, as compared with having an angle at point 20. The purpose of the bends at 20 and 22 is to provide the spring or force which accomplishes the desired splinting.

It can be seen from FIGS. 1 and 6 with the splints in place, that the open design of the splint does not interfere with movement of the fingers. Also, with the exception of the splint used as an extension splint for the thumb, as shown in FIG. 1, the pads of the fingers are left free during the splinting of the fingers. This represents a considerable convenience for using the hand while wearing the splints.

It is of particular note that the splinting of the thumb is accomplished without need for restricting the metacarpal or carpo-metacarpal joints, which have been a problem with prior art devices. Such devices require some attachment to the wrist or back of the hand.

The cushioned pads which are preferably of a heat sealed polyethylene foam which completely seals the terminal arm support sections and the central section, avoid undue pressure at the points of finger contact. This contributes to comfort to the patient and also allows for easy cleaning of the splint. By confining the cushioned pads only to the points of contact, it is possible to maintain a light weight open design permitting greater freedom of movement, not only for the splinted finger, but also for the uninvolved fingers of the hand.

Other advantages include the fact that the splints can be worn singly or all of the fingers of the hand can be splinted at the same time, as desired. Similarly, it is possible by proper bending of the splint, to use the splint as an extension splint on one finger while using another splint as a flexion splint on another adjacent finger if desired.

The ability to use the same basic splint for flexion and extensive splinting merely by changing the angles 20 and 22 of the arms 16 of the splint represents a significant cost reduction. Thus, simply by flipping the splint so that the pads 18 are on the bottom of the finger with the appropriate bending of the arms at points 20 and 22, you have an extension splint 12 as shown in FIG. 1. By turning it again, so that the pads 18 are on the top of the finger with the appropriate bending of the angles 20 and 22, you have a flexion splint 13 as shown in FIG. 6.

While the center sections 14 include a broader polyethylene pad for the extension splint 12, this is not critical. It is possible for the narrower padding which is used on the flexion splint alone to be used for both types of splinting. The narrower section provides greater movement to the finger for the flexion splint 13, but can also be used though not as preferred for the extension splint 12. Further, the adjustable nature of the splint allows for a standardized splint to be made which can then be personally tailored or fitted to each individual person without the necessity of costly customized fabrication. The fitting of the splint can be done by relatively unskilled persons, so that a great deal of expertise is not required. Thus, any person working in the art can quickly and easily be an expert at fitting the splint to a finger by utilizing the adjustable splint of the invention. Further corrections in fit during the course of treatment are also easily made as discussed previously.

Various modifications are contemplated and may be resorted to without departing from the spirit and scope of the invention as defined in the following claims.

I claim:

1. An adjustable finger splint which permits limited movement comprising:

an elongated central section having a first and a second end, said central section being concave lengthwise such that when said central section is mounted on one of the dorsal and ventral surfaces of a finger across the width of the finger and at the proximal interphalangeal joint, said central section will fit along the transverse circumferential curve of the finger;

a first elongated arm having a proximal and a distal end, said proximal end of said first arm being connected to said first end of said central section;

a second elongated arm having a proximal end and a distal end, said distal end of said second arm being connected to said second end of said central section;

said first and second arms being sized and positioned such that when said central section is mounted on one of the dorsal and ventral surfaces of a finger across the width of the finger and at the proximal interphalangeal joint, said first arm extends along one side of the finger to a point adjacent the tip of the finger and said second arm extends along the other side of the finger in a direction opposite to the direction of extension of said first arm to a point adjacent the base of said finger;

a first elongated support connected at one end to said distal end of said first arm, said first support extending in a direction substantially perpendicular to said first arm such that when said central section is mounted on one of the dorsal and ventral surfaces of a finger across the width of the finger and at the proximal interphalangeal joint, said first support is in a position to hold and support a portion of the finger adjacent the tip of the finger on the side of the finger which is opposite to that being held by said central section;

a second elongated support connected at one end to said proximal end of said second arm, said second support extending in a direction substantially perpendicular to said second arm such that when said central section is mounted on one of the dorsal and ventral surfaces of a finger across the width of the finger and at the proximal interphalangeal joint, said second support is in a position to hold and support a portion of the finger adjacent the base of the finger on the side of the finger which is opposite to that being held by said central section;

said central section and said first and second arm being formed of a continuous resilient spring material;

said splint being otherwise open along its length to permit said splint to be readily mounted and removed;

said arms being bent and bendable along their length in a direction opposite to the direction of the curve of the central section to permit adjustment of the forces applied to a finger.

2. An adjustable finger splint as claimed in claim 1 wherein:

said resilient material of which the splint is formed is a spring wire.

3. An adjustable finger splint as claimed in claim 2 wherein:

said splint is formed of a continuous length of spring wire and wherein said support pieces extending from said arms are formed into a curved closed form substantially rectangular piece.

4. An adjustable finger splint as claimed in claim 3 wherein:

said arms are further angled laterally toward said central bridging section to improve the conformation and holding capacity of said support pieces.

5. An adjustable finger splint as claimed in claim 4 wherein:

said central section and said elongated support s are covered with a flexible cushioning material and said exposed wire is encased in a flexible plastic sleeve.

6. An adjustable finger splint as claimed in claim 5 wherein:

said flexible plastic sleeve is of teflon;

said cushioning material is a heat sealed polyethylene foam; and, said spring wire is spring steel.

7. An adjustable finger splint as claimed in claim 6 wherein:

said arms have an angle substantially at the midpoint of the length thereof to give a wide "V" configuration to the arms.

* * * * *